US00PP26810P3

(12) United States Plant Patent
Pavlich

(10) Patent No.: US PP26,810 P3
(45) Date of Patent: Jun. 7, 2016

(54) ***BEGONIA* PLANT NAMED 'ENCHANTED SUNRISE'**

(50) Latin Name: ***Begonia* hybrid**
Varietal Denomination: Enchanted Sunrise

(71) Applicant: Terra Nova Nurseries, Inc., Canby, OR (US)

(72) Inventor: John C. Pavlich, East Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 106 days.

(21) Appl. No.: 14/121,787

(22) Filed: Oct. 17, 2014

(65) Prior Publication Data
US 2016/0113180 P1 Apr. 21, 2016

(51) Int. Cl.
*A01H 5/02* (2006.01)

(52) U.S. Cl.
USPC ..... Plt./343

(58) Field of Classification Search
USPC ..... Plt./343
See application file for complete search history.

*Primary Examiner* — Susan McCormick Ewoldt
(74) *Attorney, Agent, or Firm* — Klarquist Sparkman, LLP

(57) ABSTRACT

A new and distinct form of *Begonia* plant characterized by attractive dark chocolate brown leaves with green veins, numerous large salmon flowers, an upright habit when young, becoming decumbent with maturity, an extremely long bloom time, a caudiciform base, and excellent vigor.

1 Drawing Sheet

Botanical denomination: *Begonia* hybrid.
Variety designation: 'Enchanted Sunrise'.

BACKGROUND

The present invention relates to a new and distinct cultivar of *Begonia*, of the family Begoniaceae, and given the cultivar name, 'Enchanted Sunrise'. The new cultivar originated from a cross between a Nonstop™ Mocca Mix *Begonia*, an unpatented tuberous *Begonia*, as the seed parent and *Begonia boliviensis*, an unpatented tuberous *Begonia*, as the pollen parent. This selection is uniquely characterized by:

1. attractive dark chocolate brown leaves with green veins,
2. numerous large salmon flowers,
3. an upright habit when young, becoming decumbent with maturity,
4. an extremely long bloom time,
5. a caudiciform base, and
6. excellent vigor.

Compared to the seed parent, a Nonstop™ Mocca *Begonia*, the new cultivar has a larger habit with smaller and more numerous flowers that bloom over a much longer period.

Compared to the pollen parent, *Begonia boliviensis*, the new cultivar has larger, darker leaves, larger flowers that are salmon rather than red, and longer bloom time.

Compared to the salmon flowered Rieger *Begonias* (*Begonia×hiemalis*), unpatented, the new cultivar has dark foliage with green veins rather than green leaves.

Compared to its sibling 'Enchanted Evening' U.S. Plant Pat. No. 25,512, it has a slightly darker leaf with a brighter green vein and salmon rather than coral pink flowers.

The new variety has been reproduced only by asexual propagation (leaf and stem cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of an eight month old 'Enchanted Sunrise' plant of the new cultivar in a one gallon pot in a warm greenhouse in October in full bloom in Canby, Oreg.

FIG. 2 shows the whole 'Enchanted Sunrise' plant.

DETAILED PLANT DESCRIPTION

The following is a detailed description of the new *Begonia* cultivar based on observations of 9-month-old specimens grown in one gallon containers in a warm greenhouse in November in Canby, Oreg. The color descriptions are all based on *The Royal Horticultural Society Colour Chart*, 5$^{th}$ edition, 2007.

Plant:

*Type*.—Herbaceous, caudiciform perennial.
*Form*.—Upright when young, caulescent, becoming decumbent with maturity.
*Cold hardiness*.—USDA Zone 10.
*Size*.—Grows to 22 cm tall and 65 cm wide.
*Roots and rooting*.—Roots appear on leaf cuttings in 2 weeks; fine, fibrous, and white in color.
*Vigor*.—Excellent.

Stem:

*Type*.—Upright in the first season, becoming decumbent with age.
*Size*.—Grows to 35 cm long and 1 cm wide without branching.
*Internodes*.—From 15 mm to 4 cm long.
*Lateral branches*.—None.
*Surface*.—Pubescent.

*Color*.—Between Yellow Green 152A and 158A where shaded darkening to between Brown N199B and Grey-Brown 199A.

Leaf:

*Type*.—Simple.

*Arrangement*.—Alternate.

*Number*.—About 150.

*Shape*.—Obliquely ovate to lanceolate.

*Margins*.—Crenate, slightly undulate.

*Apex*.—Acuminate.

*Base*.—Oblique and cordate.

*Venation*.—Palmate, Green N138A topside, bottom side Green N138B.

*Blade size*.—Grows to 7.8 cm wide and 12.5 cm long.

*Leaf strength*.—Excellent, tough, leathery.

*Surface texture*.—Sparsely pubescent on top and glabrous on bottom.

*Stipules*.—Deciduous, ovate, 7 mm long and 5 mm wide, apex acute and cuspidate, entire, base clasping, both sides pubescent, both sides Yellow Green 148B with base Greyed Purple 187B.

*Petiole description*.—Grows to 7 cm long and 3 mm wide, succulent, pubescent, color closest to Greyed Orange 177B.

*Leaf color*.—Top side closest to Greyed Purple N186B with veins Green N138A; bottom side closest to Greyed Purple 187B, but duller, with veins Green N138B.

Inflorescence:

*Type*.—Axillary, bisexual, cymose.

*Number of flowers per cyme*.—2 to 3.

*Peduncle description*.—Grows 9 cm long and 3 mm wide, pubescent, of good strength, Yellow Green 152B tinted Greyed Orange 174A on top side in higher light; with 2 opposite, dehiscent petiolate leaf-bracts below each cyme, broadly ovate to orbicular, cupped and overlapping, each grow to 13 mm wide and 10 mm long, margins serrate and ciliate, tip obtuse, base clasping, both sides glabrous, both sides Yellow Green 147C.

*Pedicel description*.—Grow to 40 mm long, 2 mm wide, of good strength, pubescent, Greyed Orange 170C.

*Bloom period*.—Late winter to fall in Canby, Oreg.

Flower bud:

*Size*.—Grows to 34 mm long and 30 mm wide prior to opening.

*Shape*.—Round to obovate disc.

*Surface texture*.—Glabrous.

*Color*.—Red 38A on top ⅔ and White NN155A on bottom ⅓ of tepal area, Yellow Green 145B on ovary.

Flower:

*Type*.—Monoecious, bilaterally symmetrical.

*Pistillate flower*.—Grows from 5 cm to 7.5 cm wide and 2 cm to 3 cm deep; 6 fleshy tepals, each grows to 4 cm long and 2.5 mm wide, obovate, tip obtuse to acute, base cuneate, margins entire, glabrous on both sides, top and bottom side closest to Red 37B; 1 pistil, 25 mm long, ovary to 38 mm wide and 20 mm deep, three-winged, in unequal sizes, Yellow Green 145A tinted Orange Red 31C on wings, style 3-branched, each 3 mm deep and 1.5 mm wide, Orange Red 31A, stigma 2-branched and twisted, stigma branch 5 mm deep and 6 mm wide overall, Yellow Orange 22A.

*Staminate flower*.—2 cm to 3 cm deep and 7 cm to 10.5 cm wide, glabrous and Red 37A on both sides; 2 outer tepals, 46 mm to 54 mm long and 35 mm wide, oblong to obovate, margin entire, tip obtuse, base cuneate; 2 inner tepals (may have up to 6 smaller), grows to 56 mm long and 30 mm wide, obovate, margin entire, tip obtuse, base attenuate; stamen many in a globular head 17 mm in long and 10 mm deep, filaments 7 to 15 mm long, Yellow 2D, anthers 1 mm long and Yellow 22A, pollen Yellow 19A.

*Fragrance*.—None.

*Lastingness*.—A cyme blooms for about 2 weeks on the plant, flowers are self-cleaning.

Fruit and seed: None seen.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

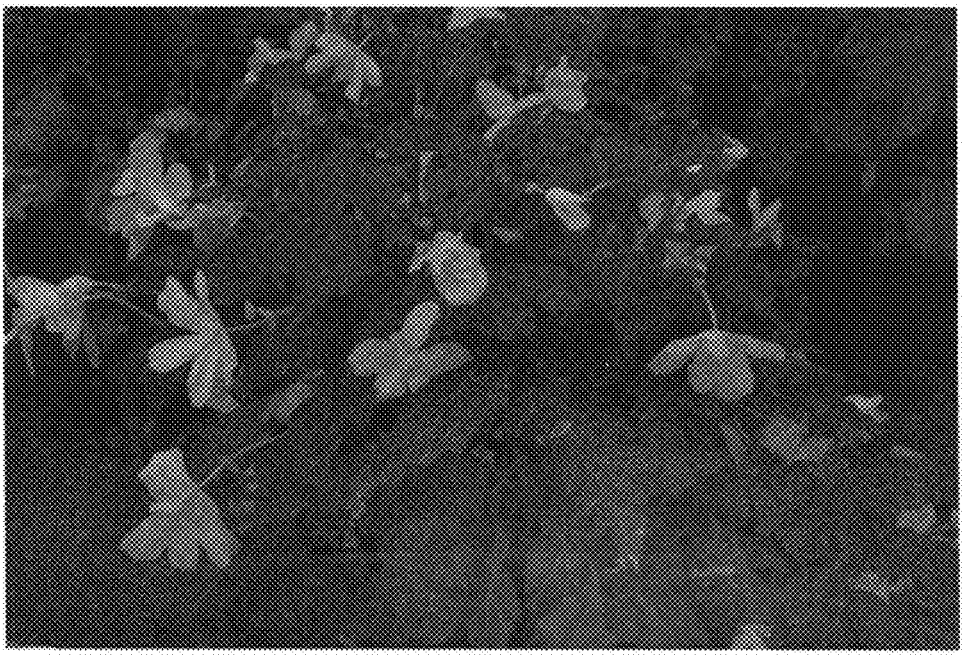

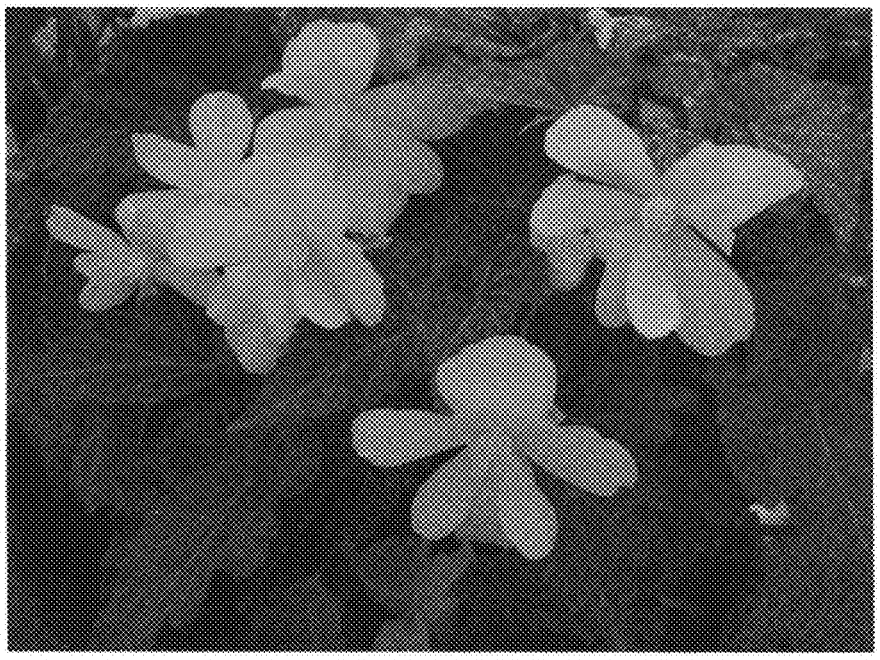
FIG. 1 above, FIG. 2 below